US011116501B1

(12) United States Patent
Marecki

(10) Patent No.: US 11,116,501 B1
(45) Date of Patent: Sep. 14, 2021

(54) SURGICAL HANDLE ARTICULATION ASSEMBLIES

(71) Applicant: Lexington Medical, Inc., Billerica, MA (US)

(72) Inventor: Andrew Marecki, West Boylston, MA (US)

(73) Assignee: Lexington Medical, Inc., Billerica, MA (US)

( * ) Notice: Subject to any disclaimer, the term of this patent is extended or adjusted under 35 U.S.C. 154(b) by 0 days.

(21) Appl. No.: 16/845,217

(22) Filed: Apr. 10, 2020

(51) Int. Cl.
*A61B 17/072* (2006.01)
*A61B 17/068* (2006.01)
*A61B 17/00* (2006.01)
*A61B 17/29* (2006.01)

(52) U.S. Cl.
CPC .... *A61B 17/0686* (2013.01); *A61B 17/07207* (2013.01); *A61B 17/068* (2013.01); *A61B 17/072* (2013.01); *A61B 2017/0046* (2013.01); *A61B 2017/00367* (2013.01);
(Continued)

(58) Field of Classification Search
CPC . A61B 17/068; A61B 17/0686; A61B 17/072; A61B 17/07207; A61B 17/2909; A61B 2017/00367; A61B 2017/07214; A61B 2017/07271; A61B 2017/292; A61B 2017/2913; A61B 2017/2927; A61B 2017/2946; G05G 1/08
USPC .............. 227/19, 176.1, 175.1, 175.2, 180.1; 606/1, 139, 205, 219; 74/527, 553; 200/419, 47, 336, 153 L, 172 R
See application file for complete search history.

(56) References Cited

U.S. PATENT DOCUMENTS

| 3,517,570 A * | 6/1970 | Kolb | G05G 1/10 |
| | | | 74/527 |
| RE28,932 E | 8/1976 | Noiles et al. | |
| 4,737,608 A | 4/1988 | Jones | |

(Continued)

FOREIGN PATENT DOCUMENTS

| EP | 1563791 | 8/2005 |
| EP | 1563792 | 8/2005 |

(Continued)

OTHER PUBLICATIONS

International Searching Authority., International Search Report and Written Opinion dated Oct. 22, 2018 for PCT Application No. PCT/US2018/038909, Filed Jun. 22, 2018, 10 pages.
(Continued)

*Primary Examiner* — Scott A Smith
(74) *Attorney, Agent, or Firm* — Brooks, Cameron & Huebsch, PLLC

(57) ABSTRACT

The present disclosure includes apparatuses for a surgical handle assembly. An example apparatus includes a reloadable cartridge assembly and a surgical handle assembly including an articulation assembly configured to maintain the reloadable cartridge assembly in a first operation position, the articulation assembly comprising a knob in a first position, a lock core coupled to the knob, a housing, a first roller and a second roller, and a first spring, wherein the first roller is positioned on a first end of the first spring and the second roller is positioned on a second end of the first spring, and wherein the first spring is configured to bias the first roller and the second roller between the lock core and the housing to maintain the knob in the first position.

20 Claims, 13 Drawing Sheets

(52) U.S. Cl.
CPC .............. *A61B 2017/07271* (2013.01); *A61B 2017/2927* (2013.01); *A61B 2017/2946* (2013.01)

(56) References Cited

U.S. PATENT DOCUMENTS

| | | | |
|---|---|---|---|
| 4,978,049 A | 12/1990 | Green | |
| 5,300,081 A | 4/1994 | Young et al. | |
| 5,326,013 A | 7/1994 | Green et al. | |
| RE34,680 E | 8/1994 | Lieser | |
| 5,474,223 A | 12/1995 | Viola et al. | |
| 5,489,058 A | 2/1996 | Plyley et al. | |
| 5,489,292 A | 2/1996 | Tovey et al. | |
| 5,507,426 A | 4/1996 | Young et al. | |
| 5,522,534 A | 6/1996 | Viola et al. | |
| 5,535,935 A | 7/1996 | Vidal et al. | |
| 5,586,711 A | 12/1996 | Plyley et al. | |
| 5,588,579 A | 12/1996 | Schnut et al. | |
| 5,702,408 A * | 12/1997 | Wales | A61B 17/07207 606/139 |
| 5,713,505 A * | 2/1998 | Huitema | A61B 17/07207 227/175.1 |
| 5,758,814 A | 6/1998 | Gallagher et al. | |
| 5,762,256 A | 6/1998 | Mastri et al. | |
| 5,799,857 A | 9/1998 | Robertson et al. | |
| 5,823,066 A | 10/1998 | Huitema | |
| 5,836,503 A | 11/1998 | Ehrenfels et al. | |
| 5,862,715 A * | 1/1999 | Lemire | H01H 19/11 74/553 |
| 5,865,361 A | 2/1999 | Milliman et al. | |
| 5,901,895 A | 5/1999 | Heaton et al. | |
| 6,109,500 A | 8/2000 | Alli et al. | |
| 6,281,453 B1 | 8/2001 | Uleski | |
| 6,302,798 B1 | 10/2001 | Nakaguro | |
| 6,945,444 B2 | 9/2005 | Gresham et al. | |
| 6,957,758 B2 | 10/2005 | Aranyi | |
| 6,981,628 B2 * | 1/2006 | Wales | A61B 17/07207 227/178.1 |
| 7,044,352 B2 | 5/2006 | Shelton, IV et al. | |
| 7,044,353 B2 | 5/2006 | Mastri et al. | |
| 7,097,089 B2 | 8/2006 | Marczyk | |
| 7,143,923 B2 | 12/2006 | Shelton, IV et al. | |
| 7,143,924 B2 | 12/2006 | Scirica et al. | |
| 7,168,604 B2 | 1/2007 | Milliman et al. | |
| 7,225,963 B2 | 6/2007 | Scirica | |
| 7,234,624 B2 | 6/2007 | Gresham et al. | |
| 7,303,106 B2 | 12/2007 | Milliman et al. | |
| 7,325,713 B2 | 2/2008 | Aranyi | |
| 7,364,060 B2 | 4/2008 | Milliman | |
| 7,380,695 B2 | 6/2008 | Doll et al. | |
| 7,380,696 B2 | 6/2008 | Shelton, IV et al. | |
| 7,398,907 B2 | 7/2008 | Racenet et al. | |
| 7,404,508 B2 | 7/2008 | Smith et al. | |
| 7,422,136 B1 | 9/2008 | Marczyk | |
| 7,431,188 B1 * | 10/2008 | Marczyk | A61B 17/0682 227/175.1 |
| 7,455,208 B2 | 11/2008 | Wales et al. | |
| 7,490,749 B2 | 2/2009 | Schall et al. | |
| 7,494,038 B2 | 2/2009 | Milliman | |
| 7,516,877 B2 | 4/2009 | Aranyi | |
| 7,546,940 B2 | 6/2009 | Milliman et al. | |
| 7,611,038 B2 | 11/2009 | Racenet et al. | |
| 7,624,902 B2 | 12/2009 | Marczyk et al. | |
| 7,694,865 B2 | 4/2010 | Scirica | |
| 7,703,653 B2 * | 4/2010 | Shah | A61B 17/07207 227/175.2 |
| 7,780,055 B2 | 8/2010 | Scirica et al. | |
| 7,802,712 B2 | 9/2010 | Milliman et al. | |
| 7,824,426 B2 | 11/2010 | Racenet et al. | |
| 7,832,408 B2 | 11/2010 | Shelton, IV et al. | |
| 7,837,079 B2 | 11/2010 | Holsten et al. | |
| 7,845,535 B2 | 12/2010 | Scirica | |
| 7,857,187 B2 | 12/2010 | Milliman | |
| 7,870,810 B2 * | 1/2011 | Da Dalt | H01H 19/6355 74/553 |
| 7,926,692 B2 | 4/2011 | Racenet et al. | |
| 7,963,431 B2 | 6/2011 | Scirica | |
| 7,967,178 B2 | 6/2011 | Scirica et al. | |
| 7,967,180 B2 | 6/2011 | Scirica | |
| 8,020,743 B2 | 9/2011 | Shelton, IV | |
| 8,061,576 B2 | 11/2011 | Cappola | |
| 8,070,036 B1 | 12/2011 | Knodel | |
| 8,123,101 B2 | 2/2012 | Racenet et al. | |
| 8,136,712 B2 | 3/2012 | Zingman | |
| 8,141,763 B2 | 3/2012 | Milliman | |
| 8,157,148 B2 | 4/2012 | Scirica | |
| 8,235,274 B2 | 8/2012 | Cappola | |
| 8,292,157 B2 | 10/2012 | Smith et al. | |
| 8,328,822 B2 | 12/2012 | Huitema et al. | |
| 8,336,751 B2 | 12/2012 | Scirica | |
| 8,336,754 B2 | 12/2012 | Cappola et al. | |
| 8,342,378 B2 | 1/2013 | Marczyk | |
| 8,360,296 B2 | 1/2013 | Zingman | |
| 8,413,868 B2 | 4/2013 | Cappola | |
| 8,424,736 B2 | 4/2013 | Scirica et al. | |
| 8,573,460 B2 | 11/2013 | Cappola | |
| 8,573,463 B2 | 11/2013 | Scirica | |
| 8,608,043 B2 | 12/2013 | Scirica | |
| 8,622,894 B2 | 1/2014 | Banik et al. | |
| 8,684,247 B2 | 4/2014 | Scirica et al. | |
| 8,684,249 B2 | 4/2014 | Racenet et al. | |
| 8,695,865 B2 | 4/2014 | Smith et al. | |
| 8,888,814 B2 | 11/2014 | Cappola | |
| 8,910,847 B2 | 12/2014 | Nalagatla et al. | |
| 9,204,876 B2 | 12/2015 | Cappola et al. | |
| 9,364,218 B2 | 6/2016 | Scirica | |
| 9,393,016 B2 | 7/2016 | Scirica et al. | |
| 9,539,006 B2 | 1/2017 | Collings et al. | |
| 9,655,617 B2 | 5/2017 | Cappola | |
| 9,679,716 B2 * | 6/2017 | Faurie | H01H 19/54 |
| 9,861,358 B2 | 1/2018 | Marczyk et al. | |
| 9,931,739 B2 | 4/2018 | Nelson | |
| 10,383,634 B2 | 8/2019 | Shelton, IV | |
| 2001/0030219 A1 | 10/2001 | Green et al. | |
| 2004/0232199 A1 | 11/2004 | Shelton, IV et al. | |
| 2005/0006429 A1 | 1/2005 | Wales | |
| 2006/0111210 A1 | 5/2006 | Hinman | |
| 2007/0125826 A1 | 6/2007 | Shelton, IV | |
| 2007/0262116 A1 | 11/2007 | Hueil et al. | |
| 2008/0083810 A1 | 4/2008 | Marczyk | |
| 2008/0179374 A1 | 7/2008 | Beardsley et al. | |
| 2008/0179375 A1 * | 7/2008 | Scirica | A61B 17/068 227/176.1 |
| 2009/0062614 A1 | 3/2009 | Adzich et al. | |
| 2009/0206137 A1 * | 8/2009 | Hall | A61B 17/07207 227/176.1 |
| 2009/0272614 A1 | 11/2009 | Watarai | |
| 2010/0264193 A1 | 10/2010 | Huang | |
| 2011/0062211 A1 | 3/2011 | Ross | |
| 2011/0253765 A1 | 10/2011 | Nicholas | |
| 2012/0138659 A1 * | 6/2012 | Marczyk | A61B 17/07207 227/175.1 |
| 2012/0286019 A1 | 11/2012 | Hueil | |
| 2013/0092719 A1 | 4/2013 | Kostrzewski | |
| 2013/0098966 A1 | 4/2013 | Kostrzewski et al. | |
| 2013/0199327 A1 | 8/2013 | Park et al. | |
| 2013/0245676 A1 | 9/2013 | Cappola | |
| 2013/0304115 A1 | 11/2013 | Miyamoto | |
| 2014/0276949 A1 | 9/2014 | Staunton et al. | |
| 2015/0196996 A1 | 7/2015 | Nelson | |
| 2015/0342605 A1 | 12/2015 | Abbott et al. | |
| 2015/0374396 A1 | 12/2015 | Strobl | |
| 2016/0166250 A1 | 6/2016 | Marczyk | |
| 2016/0270786 A1 | 9/2016 | Scirica | |
| 2017/0000485 A1 | 1/2017 | Shelton, IV et al. | |
| 2017/0172577 A1 | 6/2017 | Wenchell et al. | |
| 2017/0281177 A1 | 10/2017 | Harris et al. | |
| 2017/0281184 A1 | 10/2017 | Shelton, IV | |
| 2017/0281220 A1 | 10/2017 | Hibner | |
| 2018/0078354 A1 | 3/2018 | Cardinale et al. | |
| 2018/0168599 A1 | 6/2018 | Bakos | |
| 2018/0289370 A1 | 10/2018 | Amariglio et al. | |
| 2018/0310935 A1 | 11/2018 | Wixey | |

(56) References Cited

U.S. PATENT DOCUMENTS

2018/0317915 A1 11/2018 McDonald, II
2018/0368832 A1 12/2018 Marecki et al.
2020/0008801 A1 1/2020 Somekh et al.

FOREIGN PATENT DOCUMENTS

| EP | 1563794 | 8/2005 |
| EP | 1709911 | 10/2006 |
| EP | 1021130 | 11/2006 |
| EP | 2253277 | 11/2010 |
| EP | 2253278 | 11/2010 |
| EP | 2886020 | 6/2015 |
| EP | 2484290 | 7/2015 |
| EP | 2311385 | 5/2017 |

OTHER PUBLICATIONS

International Searching Authority., International Search Report and Written Opinion dated Jun. 18, 2018 for PCT Application No. PCT/US2018/025988, Filed Apr. 4, 2018, 9 pages.
International Searching Authority., International Search Report and Written Opinion dated Oct. 4, 2019 for PCT Application No. PCT/US2019/040315, Filed Jul. 2, 2019, 9 pages.
International Searching Authority., International Search Report and Written Opinion dated Jun. 28, 2021 for PCT Application No. PCT/US2021/025899 Filed Apr. 6, 2021, 7 pages.

\* cited by examiner

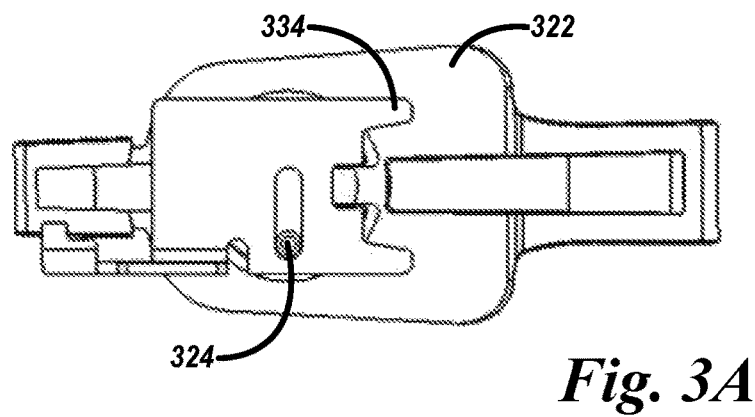
*Fig. 3A*
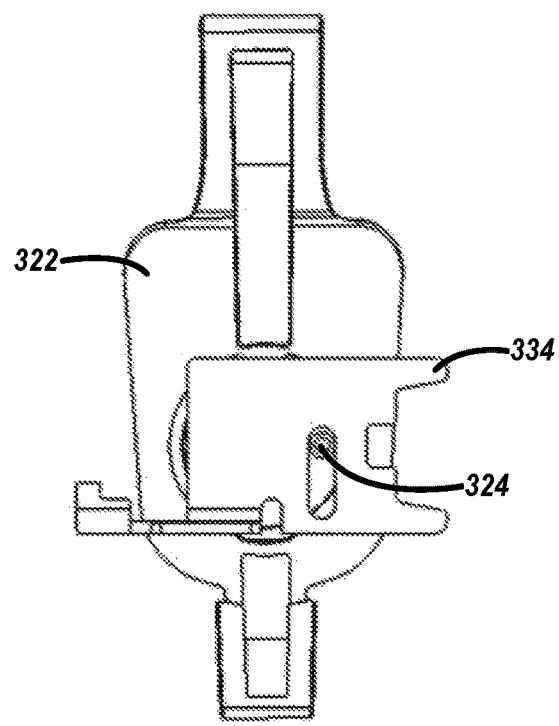 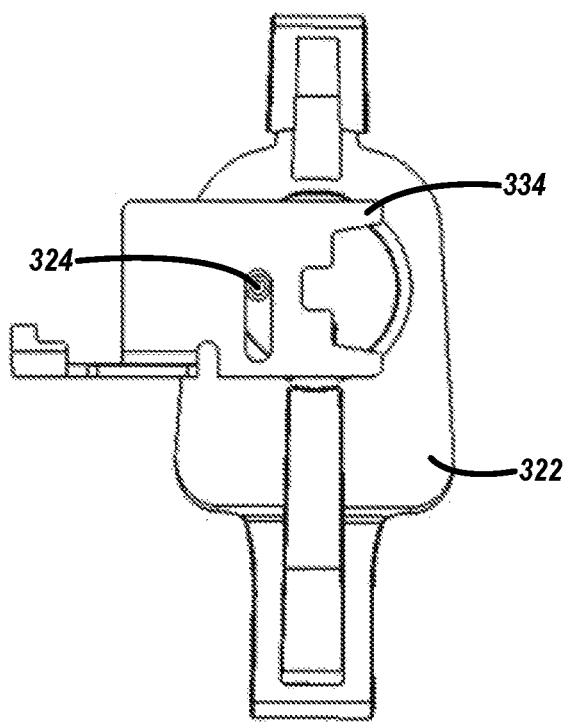
*Fig. 3B*  *Fig. 3C*

SURGICAL HANDLE ARTICULATION ASSEMBLIES

TECHNICAL FIELD

The present disclosure relates generally to a surgical handle assembly, and more particularly, to articulation assemblies for a surgical handle assembly.

BACKGROUND

A surgical handle assembly can be used in a number of surgical devices. One example includes use as a surgical stapler. A surgical stapler is a fastening device used to clamp tissue between opposing jaw structures to join tissue using surgical fasteners. Surgical staplers can include two elongated members used to clamp the tissue. One of the elongated members can include one or more reloadable cartridges and the other elongated member can include an anvil that can be used to form a staple when driven from the reloadable cartridge. A surgical stapler can receive one or more reloadable cartridges. An example of reloadable cartridges can include having rows of staples having a linear length. For example, a row of staples can have a linear length between 30 mm and 60 mm. A staple can be ejected by actuation of a movable handle member that is a part of the surgical handle assembly of the surgical stapler.

BRIEF DESCRIPTION OF THE DRAWINGS

FIG. 3A is a schematic diagram of an articulation assembly including a knob, a cam, and a sliding link in a 0 degree knob position in accordance with a number of embodiments of the present disclosure.

FIG. 3B is a schematic diagram of an articulation assembly including a knob, a cam, and a sliding link in a 90 degree knob position in accordance with a number of embodiments of the present disclosure.

FIG. 3C is a schematic diagram of an articulation assembly including a knob, a cam, and a sliding link in a −90 degree knob position in accordance with a number of embodiments of the present disclosure.

DETAILED DESCRIPTION

Figure 1:
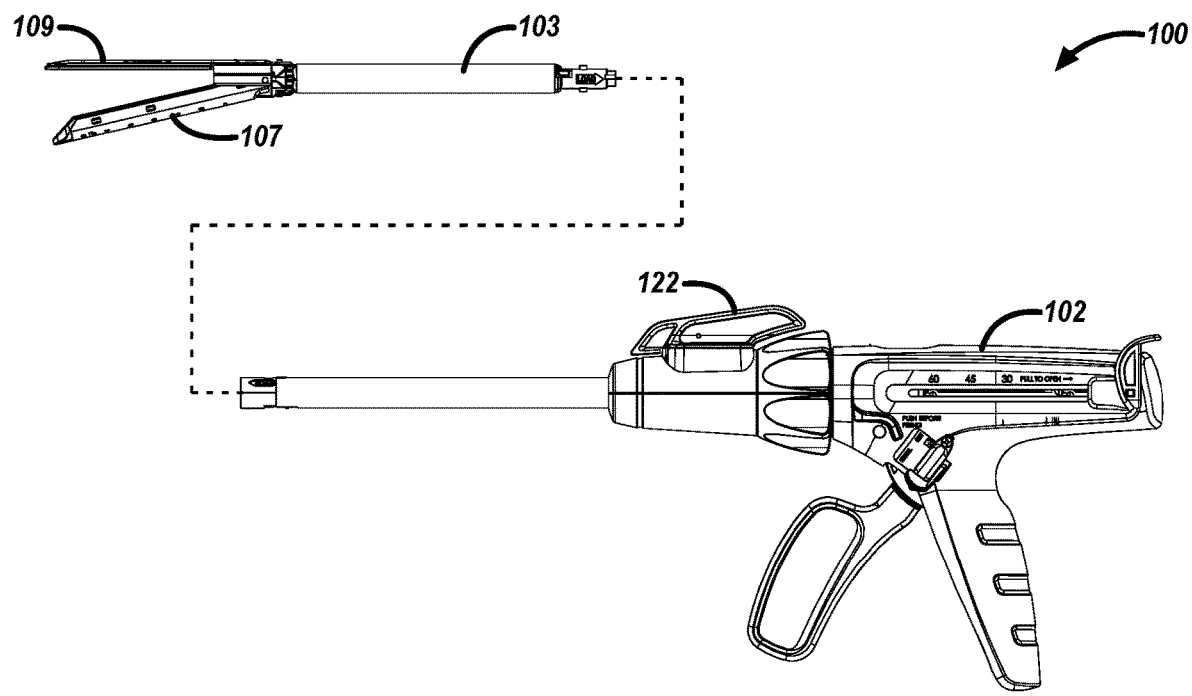
FIG. 1 is a schematic diagram of an apparatus including a surgical handle assembly and a reloadable cartridge assembly in accordance with a number of embodiments of the present disclosure.

The present disclosure includes apparatuses and methods for a surgical stapler. An example apparatus includes a reloadable cartridge assembly and a surgical handle assembly including an articulation assembly configured to maintain the reloadable cartridge assembly in a first operation position. In some examples, the articulation assembly can include a knob in a first position, a lock core coupled to the knob, a top housing, a first roller and a second roller, and a first spring. The first roller can be positioned on a first end of the first spring and the second roller can be positioned on a second end of the first spring and the first spring can be configured to bias the first roller and the second roller between the lock core and the top housing to maintain the knob in the first position.

In a number of embodiments, the articulation assembly is configured to maintain the reloadable cartridge assembly in one of a plurality of operation positions. For example, the articulation assembly can be configured to maintain the reloadable cartridge assembly in the first operation position. In some examples, the reloadable cartridge assembly can be configured to rotate about an axis of a particular plane from the first operation position to a second operation position. The articulation assembly can be configured to actuate the reloadable cartridge assembly from the first operation position to the second operation position.

In a number of embodiments, the articulation assembly can further include a cam coupled to the lock core. The cam can include a pin member that moves linearly in response to the cam rotating. The pin member can be positioned within a slot of a sliding link and the sliding link can be coupled to an articulation arm. The sliding link and the articulation arm can move linearly in response to the pin member moving linearly.

The articulation arm can be coupled to the reloadable cartridge assembly. The reloadable cartridge assembly can rotate from a first operation position to a second operation position in response to the articulation arm moving linearly, as a result of the user rotating the knob.

In the following detailed description of the present disclosure, reference is made to the accompanying drawings that form a part hereof, and in which is shown by way of illustration how one or more embodiments of the disclosure may be practiced. These embodiments are described in sufficient detail to enable those of ordinary skill in the art to practice the embodiments of this disclosure, and it is to be understood that other embodiments may be utilized and that process, electrical, and structural changes may be made without departing from the scope of the present disclosure.

As used herein, designators such as "N", "M", "P", "Q", "R", "S", "T", "V", "X", "Y", "Z", etc., particularly with respect to reference numerals in the drawings, indicate that a number of the particular feature so designated can be included. It is also to be understood that the terminology used herein is for the purpose of describing particular embodiments only and is not intended to be limiting. As used herein, the singular forms "a", "an", and "the" can include both singular and plural referents, unless the context clearly dictates otherwise. In addition, "a number of", "at least one", and "one or more" (e.g., a number of pivot points) can refer to one or more pivot points, whereas a "plurality of" is intended to refer to more than one of such things. Furthermore, the words "can" and "may" are used throughout this application in a permissive sense (i.e., having the potential to, being able to), not in a mandatory sense (i.e., must). The term "include," and derivations thereof, means "including, but not limited to". The terms "coupled" and "coupling" mean to be directly or indirectly connected physically or for access to and movement of the apparatus, as appropriate to the context.

The figures herein follow a numbering convention in which the first digit or digits correspond to the figure number and the remaining digits identify an element or component in the figure. Similar elements or components between different figures may be identified by the use of similar digits. For example, 222 may reference element "22" in FIG. 2, and a similar element may be referenced as 322 in FIG. 3A. As will be appreciated, elements shown in the various embodiments herein can be added, exchanged, and/or eliminated so as to provide a number of additional embodiments of the present disclosure. In addition, the proportion and/or the relative scale of the elements provided in the figures are intended to illustrate certain embodiments of the present disclosure and should not be taken in a limiting sense.

FIG. 1 is a schematic diagram of an apparatus 100 including a surgical handle assembly 102 and a reloadable cartridge assembly 103 in accordance with a number of embodiments of the present disclosure. In the example, the apparatus 100 can be a surgical stapler, for example.

As shown in the example of FIG. 1, the reloadable cartridge assembly 103, e.g. a disposable loading unit, can be releasably secured to a distal end of an elongated body of the surgical handle assembly 102. In this example, the reloadable cartridge assembly 103 can include a first elongated member 107 and a second elongated member 109 that can be used to clamp tissue. One of the elongated members can house one or more staple cartridges. The other elongated member can have an anvil that can be used to form a staple when driven from the staple cartridge. As mentioned, an apparatus 100 can receive reloadable cartridge assemblies having rows of staples. In a number of embodiments, third party reloadable cartridge and/or reloadable cartridge assemblies may be used with the surgical handle assembly 102 and embodiments of surgical handle assembly 102 may be configured to receive the same.

The reloadable cartridge assembly 103 can be actuated using a knob 122 to reach a stapling site and position the reloadable cartridge assembly 103 at a particular angle for stapling. The knob 122 can be configured to actuate rotationally and at least a portion of the reloadable cartridge assembly 103 (e.g., elongated members 107 and 109) can rotate about an axis of a particular plane in response to the knob 122 being actuated rotationally by a user.

Figure 2:
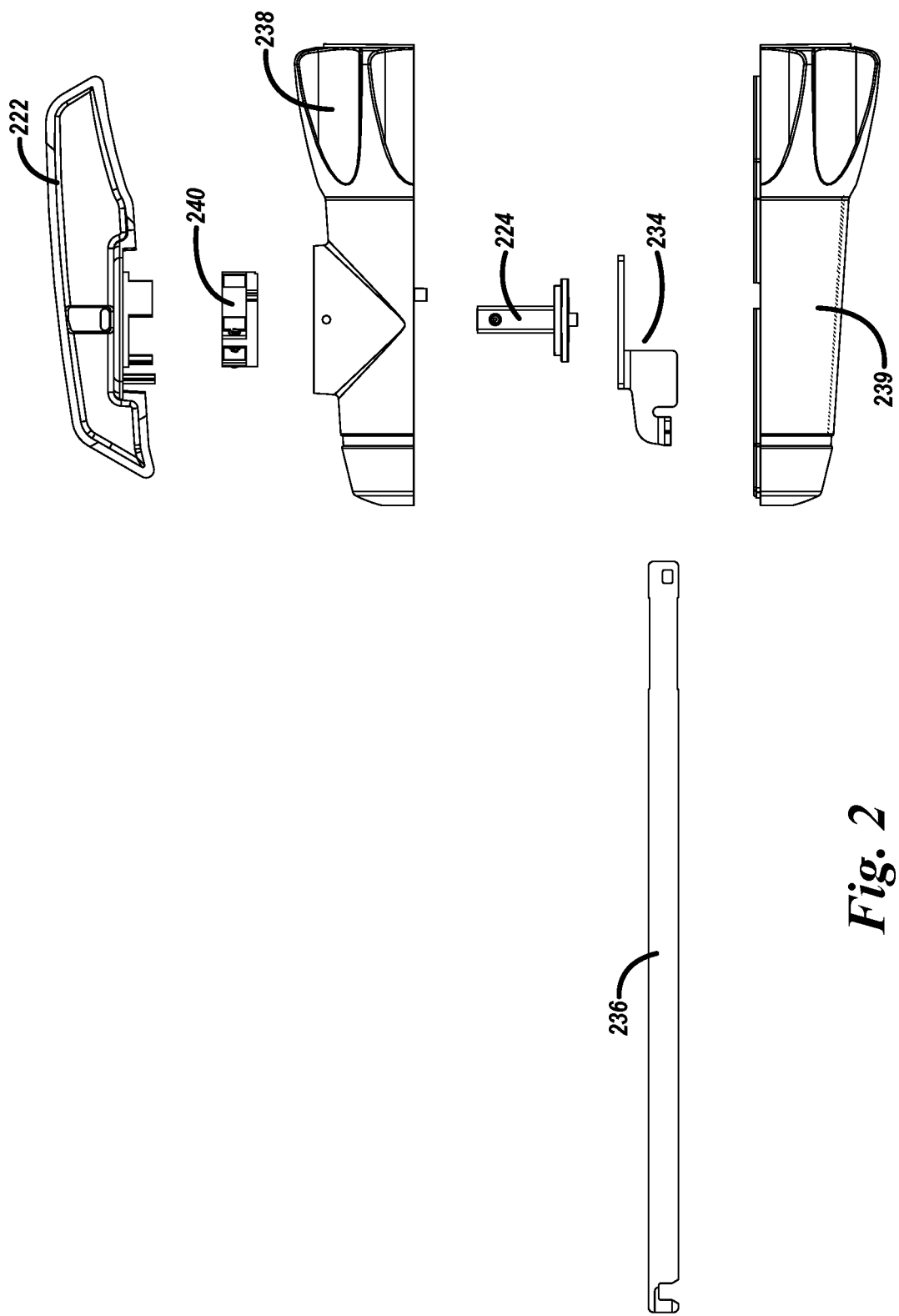
FIG. 2 is an exploded view of a schematic diagram of an articulation assembly in accordance with a number of embodiments of the present disclosure.

FIG. 2 is an exploded view of a schematic diagram of an articulation assembly in accordance with a number of embodiments of the present disclosure. In some examples, the articulation assembly can include a knob 222, a cam 224, a lock core 240, a sliding link 234, an articulation arm 236, a top housing 238, and a bottom housing 239.

The knob 222 can be coupled to the cam 224 and the lock core 240 can be coupled to the knob 222, the top housing 238, and the cam 224. In some examples the knob 222 can be coupled to the cam 224 via a spring pin. The lock core 240 can actuate rotationally in response to the knob 222 being rotationally actuated by a user which in turn rotationally actuates cam 224.

In a number of embodiments, the cam 224 is coupled to a sliding link 234. The cam 224 can include a pin member to move linearly within a slot of the sliding link 234. The sliding link 234 can be configured to move in a linear direction in response to the cam 224 actuating rotationally. In some examples, the sliding link 234 can be coupled to an articulation arm 236.

The articulation arm 236 can move in a linear direction in response to the sliding link 234 moving in the linear direction. In some examples, the articulation arm 236 and the sliding link 234 can move in a linear distal direction in response to the lock core 240, cam 224, and knob 222 rotating counterclockwise. The articulation arm 236 and the sliding link 234 can move in a linear proximal direction in response to the lock core 240, cam 224, and knob 222 rotating clockwise.

The articulation arm 236 can be coupled to the reloadable cartridge assembly (e.g., reloadable cartridge assembly 103 in FIG. 1). The reloadable cartridge assembly can rotate counterclockwise in response to the articulation arm 236 moving in the linear distal direction as a result of the user rotating the knob 222 in a counterclockwise direction. The reloadable cartridge assembly can rotate clockwise in response to the articulation arm 236 moving in the linear proximal direction as a result of the user rotating the knob 222 in a clockwise direction.

FIG. 3A is a schematic diagram of an articulation assembly including a knob 322, a cam 324, and a sliding link 334 in a 0 degree knob position in accordance with a number of embodiments of the present disclosure.

As previously discussed, the cam 324 can include a pin member. The pin member can be a part of the cam 324 or coupled to the cam 324. The pin member can be positioned within a slot of the sliding link 334. The location of the pin member on the cam 324 can determine whether the reloadable cartridge assembly (e.g., reloadable cartridge assembly 103 in FIG. 1) rotates counterclockwise or clockwise in response to the user rotating the knob 322 counterclockwise or clockwise.

For example, with the location of the pin member of the cam 324 shown in FIG. 3A, the sliding link 334 can move in a linear distal direction causing the reloadable cartridge assembly (e.g., reloadable cartridge assembly 103 in FIG. 1) to move counterclockwise in response to the knob 322 rotating counterclockwise and the sliding link 334 can move in a linear proximal direction causing the reloadable cartridge assembly to move clockwise in response to the knob 322 rotating clockwise. In some examples, the pin member of the cam 324 can be located in a location on the cam 324, such that the reloadable cartridge assembly (e.g., reloadable cartridge assembly 103 in FIG. 1) will rotate clockwise in response to the knob 322 rotating counterclockwise and the reloadable cartridge assembly will rotate counterclockwise in response to the knob 322 rotating clockwise.

FIG. 3B is a schematic diagram of an articulation assembly including a knob 322, a cam 324, and a sliding link 334 in a 90 degree knob position in accordance with a number of embodiments of the present disclosure.

With the location of the pin member of the cam 324 shown in FIG. 3B, the reloadable cartridge assembly (e.g., reloadable cartridge assembly 103 in FIG. 1) can be in a 45 degree operation mode in response to the knob 322 being in the 90 degree knob position. In some examples, the pin member of the cam 324 can be located in a location on the cam 324, such that the reloadable cartridge assembly (e.g., reloadable cartridge assembly 103 in FIG. 1) will be in a −45 degree operation mode in response to the knob 322 being in a 90 degree knob position.

FIG. 3C is a schematic diagram of an articulation assembly including a knob 322, a cam 324, and a sliding link 334 in a −90 degree knob position in accordance with a number of embodiments of the present disclosure.

With the location of the pin member of the cam 324 shown in FIG. 3C, the reloadable cartridge assembly (e.g., reloadable cartridge assembly 103 in FIG. 1) can be in a −45 degree operation mode in response to the knob 322 being in the −90 degree knob position. In some examples, the pin member of the cam 324 can be located in a location on the cam 324, such that the reloadable cartridge assembly (e.g., reloadable cartridge assembly 103 in FIG. 1) will be in a 45 degree operation mode in response to the knob 322 being in a −90 degree knob position.

Figure 4A:
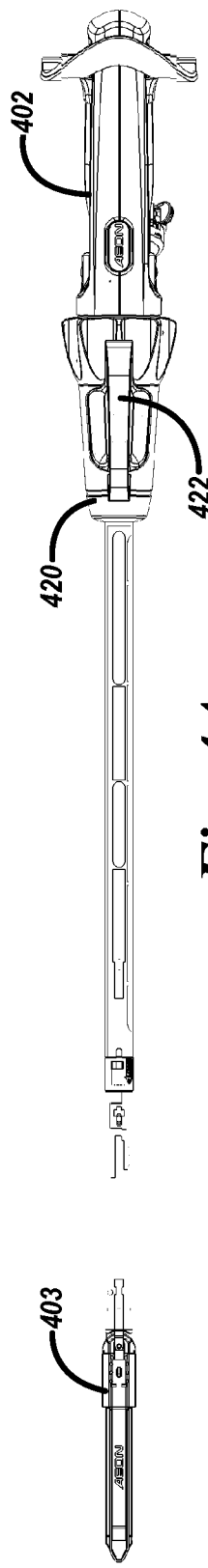
FIG. 4A is a schematic diagram of an apparatus including a surgical handle assembly apparatus including an articulation assembly and a reloadable cartridge assembly in a 0 degree operation position in accordance with a number of embodiments of the present disclosure.

FIG. 4A is a schematic diagram of an apparatus including a surgical handle assembly apparatus 402 including an articulation assembly 420 and a reloadable cartridge assembly 403 in a 0 degree operation position in accordance with a number of embodiments of the present disclosure. The articulation assembly 420 can include a knob 422.

In a number of embodiments, the articulation assembly 420 can be configured to maintain the reloadable cartridge assembly 403 in an operation position corresponding to knob 422. In this example, the knob 422 is in a 0 degree knob position. As such, the reloadable cartridge assembly 403 is in the corresponding 0 degree operation position and is maintained in the 0 degree operation position as long as the knob 422 is maintained in the 0 degree knob position.

The articulation assembly 420 can be configured to actuate the reloadable cartridge assembly 403 from a first operation position, for example a 0 degree operation position, corresponding to a first knob position, for example a 0 degree knob position, to a different operation position corresponding to a different knob position.

The reloadable cartridge assembly 403 can be actuated to any operation position totaling approximately 90 degrees. In some examples, the reloadable cartridge assembly 403 can be actuated to a number of operation positions between approximately 45 degrees and −45 degrees in response to the knob 422 being actuated to a number of knob positions between approximately 90 degrees and −90 degrees. The reloadable cartridge assembly 403 can be actuated to an operation position of 12.2, 26, −8.4, and/or −16.8 degrees, for example.

Figure 4B:
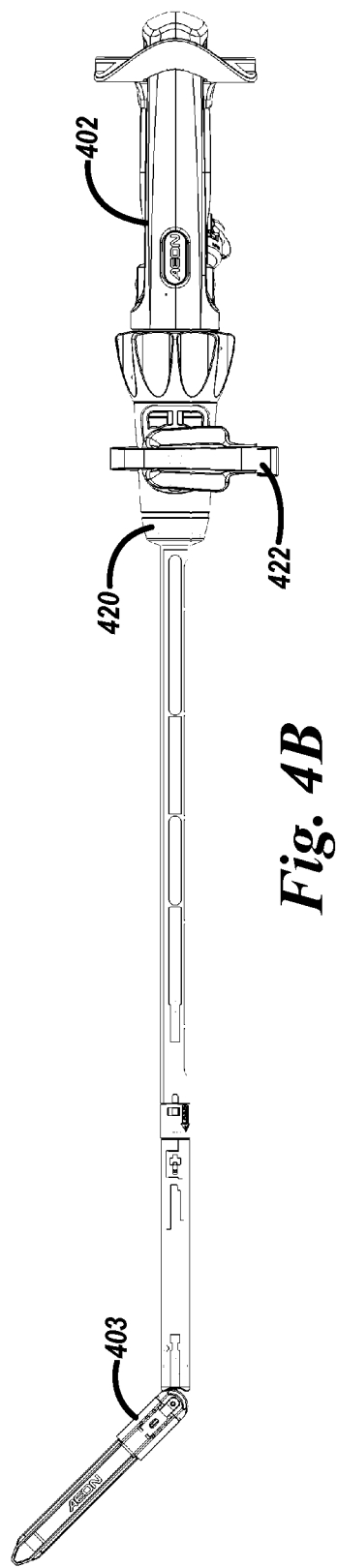
FIG. 4B is a schematic diagram of an apparatus including a surgical handle assembly apparatus including an articulation assembly and a reloadable cartridge assembly in a 45 degree operation position in accordance with a number of embodiments of the present disclosure.

FIG. 4B is a schematic diagram of an assembly apparatus including a surgical handle assembly apparatus 402 including an articulation assembly 420 and a reloadable cartridge assembly 403 in a 45 degree operation position in accordance with a number of embodiments of the present disclosure. In some examples the articulation assembly 420 can include a knob 422.

In a number of embodiments, the articulation assembly 420 can be configured to maintain the reloadable cartridge assembly 403 in an operation position corresponding to a knob position. In this example, the knob 422 is maintained in a 90 degree knob position. As such, the reloadable cartridge assembly 403 is in the corresponding 45 degree operation position and is maintained in the 45 degree operation position as long as the knob 422 is maintained in the 90 degree knob position.

The articulation assembly 420 can be configured to actuate the reloadable cartridge assembly 403 from the 45 degree operation position corresponding to a 90 degree knob position, to a different operation position corresponding to a different knob position.

Figure 4C:
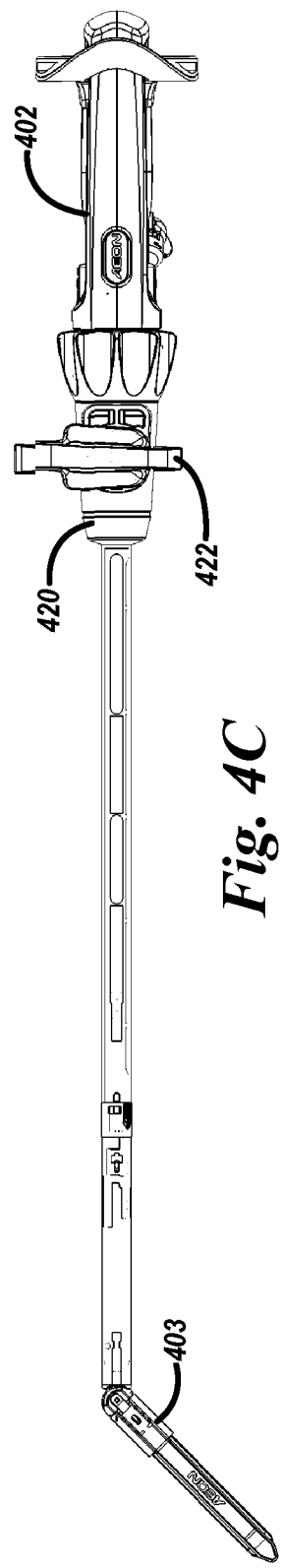
FIG. 4C is a schematic diagram of an apparatus including a surgical handle assembly apparatus including an articulation assembly and a reloadable cartridge assembly in a −45 degree operation position in accordance with a number of embodiments of the present disclosure.

FIG. 4C is a schematic diagram of an assembly apparatus including a surgical handle assembly apparatus 402 including an articulation assembly 420 and a reloadable cartridge assembly 403 in a −45 degree operation position in accordance with a number of embodiments of the present disclosure. In some examples the articulation assembly 420 can include a knob 422.

In a number of embodiments, the articulation assembly 420 can be configured to maintain the reloadable cartridge assembly 403 in an operation position corresponding to a knob position. In this example, the knob 422 is maintained in a −90 degree knob position. As such, the reloadable cartridge assembly 403 is in the corresponding −45 degree operation position and is maintained in the −45 degree operation position as long as the knob 422 is maintained in the −90 degree knob position.

In some examples, the reloadable cartridge assembly 403 can be actuated to a number of operation positions from the −45 degree operation position in response to the knob 422 being actuated by a user. The articulation assembly 420 can be configured to actuate the reloadable cartridge assembly 403 from the −45 degree operation position corresponding to the −90 degree knob position to a different operation position corresponding to a different knob position.

Figure 5:
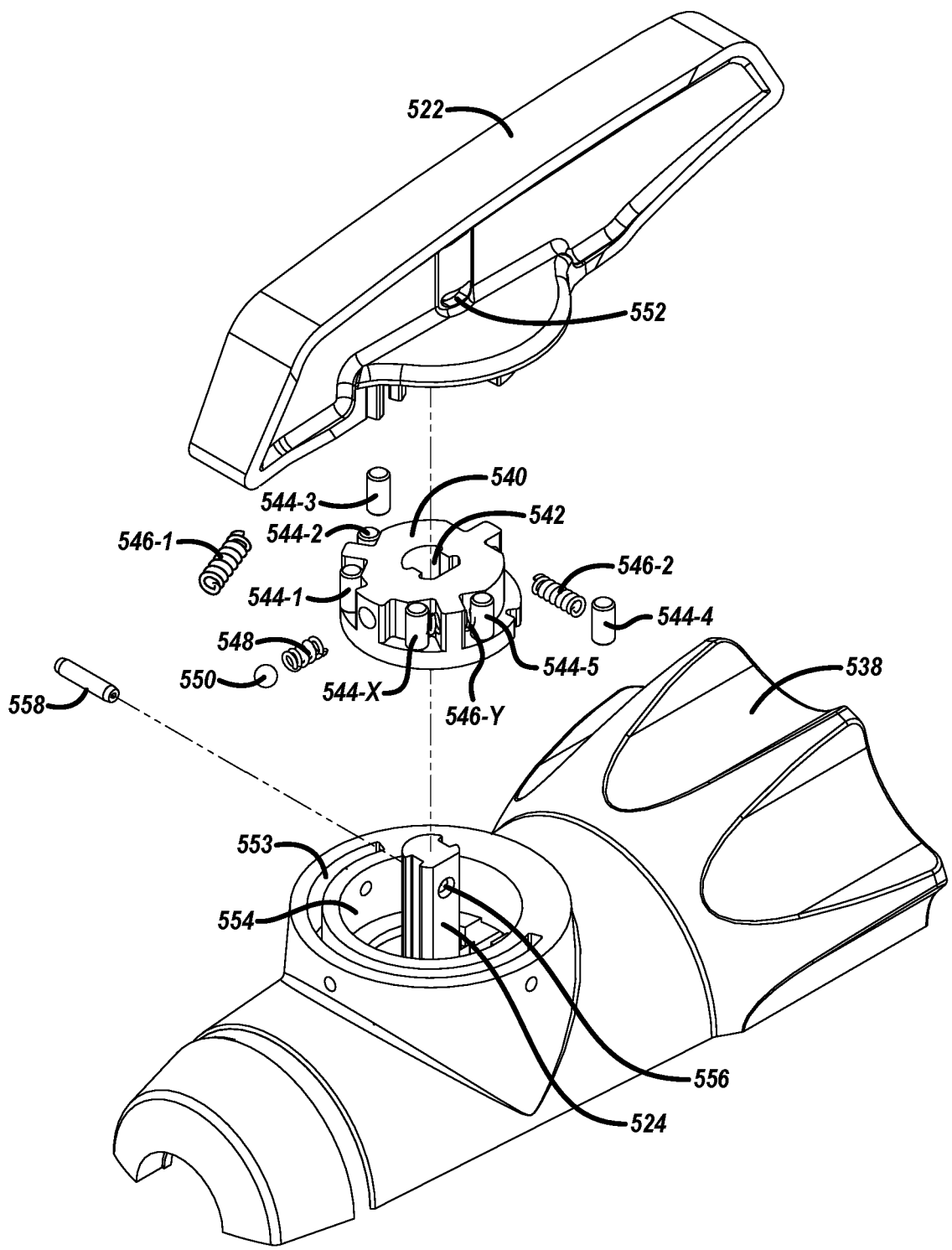
FIG. 5 is an exploded view of an articulation assembly including a knob, a lock core, a top housing, and a cam in a 0 degree knob position in accordance with a number of embodiments of the present disclosure.

FIG. 5 is an exploded view of an articulation assembly including a knob 522, a lock core 540, a top housing 538, and a cam 524 in a 0 degree knob position in accordance with a number of embodiments of the present disclosure. In some examples, the articulation assembly can further include one or more rollers 544-1, 544-2, 544-3, 544-4, 544-5, 544-X, one or more roller springs 546-1, 546-2, 546-Y, a detent spring 548, a detent sphere 550, and a spring pin 558. Although, six rollers 544-1, . . . , 544-X and three roller springs 546-1, ..., 546-Y are illustrated, an articulation assembly can include any number of rollers 544-1, ..., 544-X and any numbers of roller springs 546-1, ..., 546-Y. In some examples, the rollers 544-1, ..., 544-X can be made out of metal or plastic.

The knob 522 can include an opening 552 (e.g., a slot) and the knob 522 can be coupled to the cam 524 via a spring pin 558, for example. As will be described below, spring pin 558 keeps knob 522 attached to the shaft of cam 524 but does not interfere with the rotation of knob 522 as opening 552 allows the knob 522 to rotate without interference from pin 558.

In some examples, the lock core 540 can be coupled to the top housing 538 and cam 524 can be coupled to lock core 540. For example, when assembled, lock core 540 fits within cylindrical opening 554 of the top housing 538, the shaft of cam 524 fits within spline 542 (e.g., an opening) of lock core 540, and pin 558 is within opening 556 of cam 524 and opening 552 of the knob 522.

The top surface of top housing 538, can include a stop slot 553. Knob 522 can further include a stop tab (e.g., stop tab 662 in FIG. 6). The stop tab can be located within stop slot 553. The stop tab can limit the rotation of knob 522 in response to contacting an end of the stop slot 553.

Figure 6:
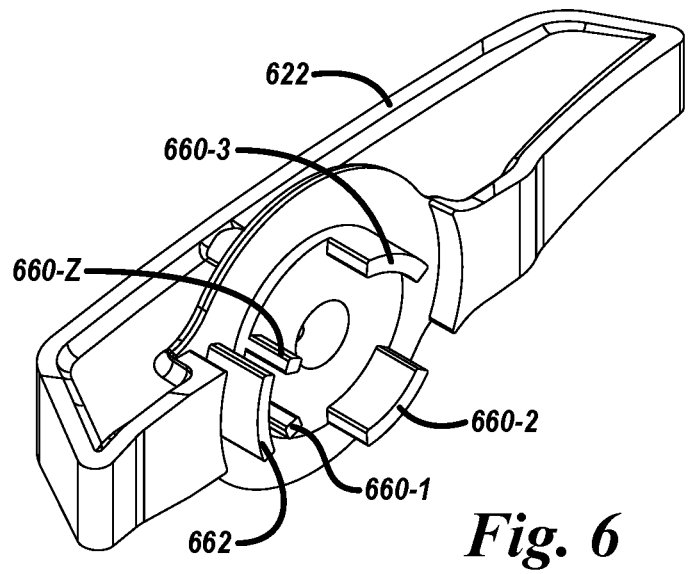
FIG. 6 is a perspective view of a knob in accordance with a number of embodiments of the present disclosure.

FIG. 6 is a perspective view of knob 622. The bottom of knob 622 can include a number of tabs 660-1, 660-2, 660-3, 660-Z (e.g., lugs or bosses). The tabs 660-1, ..., 660-Z, 662 can be a part of or coupled to knob 622. As will be further explained in FIG. 8B, one or more of tabs 660-1, ..., 660-Z can be used to contact one or more rollers (e.g., rollers 544-1, ..., 544-X in FIG. 5) in response to a rotation of knob 622.

As previously described in connection with FIG. 5, knob 622 can further include a stop tab 662. The stop tab 662 can be located within a stop slot (e.g., stop slot 553 in FIG. 5). The stop tab 662 can limit the rotation of knob 622 in response to contacting an end of the stop slot.

Figure 7A:
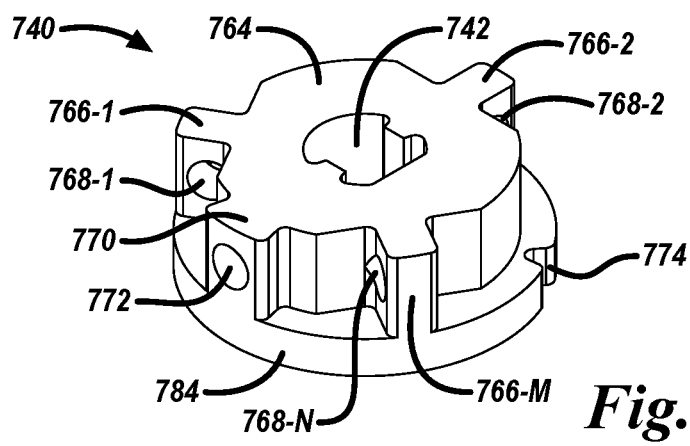
FIG. 7A is a perspective view of a lock core in accordance with a number of embodiments of the present disclosure.

FIG. 7A is a perspective view of a lock core 740 in accordance with a number of embodiments of the present disclosure. In FIG. 7A, lock core 740 includes a top portion 764, one or more spring tabs 766-1, 766-2, 766-M each including a roller spring opening 768-1, 768-2, 768-N, a detent tab 770 including a detent spring opening 772, a spline 742, and a key 774.

FIG. 7A illustrates three spring tabs 766-1, ..., 766-M, but a lock core 740 can include any number of spring tabs 766-1, ..., 766-M. Each of the one or more spring tabs 766-1, ..., 766-M can include one or more roller spring openings 768-1, ..., 768-N. A portion of one or more roller springs (e.g., roller springs 546-1, ..., 546-Y in FIG. 5) can be located within the one or more roller spring openings 768-1, ..., 768-N. The one or more roller spring openings 768-1, ..., 768-N can extend a particular distance into the one or more spring tabs 766-1, ..., 766-M or extend through the one or more spring tabs 766-1, ..., 766-M to allow a roller spring to pass through the one or more spring tabs 766-1, ..., 766-M. For example, roller spring opening 768-N can extend through spring tab 766-M and a spring (e.g., spring 546-Y in FIG. 5) can be located within roller spring opening 768-N and extend through spring tab 766-M to contact a roller (e.g., roller 544-X in FIG. 5) on a first side of spring tab 766-M and contact a roller (e.g., roller 544-5 in FIG. 5) on a second side of tab 766-M. In some examples, each of the one or more roller spring openings 768-1, ..., 768-N can extend a particular distance into the one or more spring tabs 766-1, ..., 766-M to prevent the one or more springs from extending through the one or more spring tabs 766-1, ..., 766-M and allow a first spring to extend from an opening of the one or more openings 768-1, ..., 768-N on a first side of a tab of the one or more spring tabs 766-1, ..., 766-M and a second spring to extend from an opening of the one or more openings 768-1, ..., 768-N on a second side of a tab of the one or more spring tabs 766-1, ..., 766-M.

Detent tab 770 can include detent spring opening 772. A portion of a detent spring (e.g., detent spring 548 in FIG. 5) can be located within detent spring opening 772. The detent spring can bias a detent sphere (e.g., detent sphere 550 in FIG. 5), into an opening when a knob (e.g., knob 622 in FIG. 6) is located at 0 degrees. In some examples, the knob can include one continuous tab instead of two tabs of the one or more tabs (e.g., tabs 660-1, ..., 660-Z in FIG. 6) in response to the articulation assembly not including the detent tab 770. For example, a first tab (e.g., tab 660-1 in FIG. 6) and a second tab (e.g., tab 660-Z in FIG. 6) can be combined into one tab.

Spline 742 can be an opening through lock core 740. The shaft of a cam (e.g., cam 524 in FIG. 5) can be positioned within spline 742. The cam be forced to move rotationally in response to the lock core 740 moving rotationally.

The lock core 740 can further include a key 774. The key can be a void in the lock core 740, for example, used in the manufacturing process of the articulation assembly. Using the position of key 774, either a manual or automated manufacturing system can place lock core 740 into cylindrical opening (e.g., cylindrical opening 554 in FIG. 5) in the proper orientation.

Figure 7B:
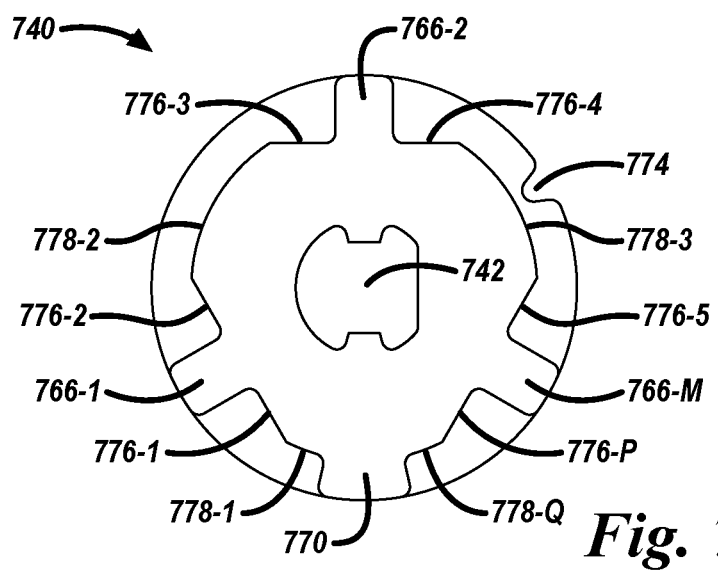
FIG. 7B is a top view of a lock core in accordance with a number of embodiments of the present disclosure.

FIG. 7B is a top view of a lock core 740 in accordance with a number of embodiments of the present disclosure. The lock core 740 includes one or more spring tabs 766-1, 766-2, 766-M, a detent tab 770, a spline 742, portions of a concentric void 778-1, 778-2, 778-3, 778-Q, and jamming surfaces 776-1, 776-2, 776-3, 776-4, 776-5, 776-P.

In this embodiment, the portions of the concentric void 778-1, ..., 778-Q can create a discontinuous cylinder with a circumference less than the inner circumference of a cylindrical opening (e.g., opening 554 in FIG. 5). Jamming surfaces 776-1, ..., 776-P can be chords of the circle corresponding to the portions of the concentric void 778-1, ..., 778-Q. When lock core 740 is placed in the cylindrical opening, the depth from the surface of the cylindrical opening to the surface of the jamming surfaces 776-1, ..., 776-P range from being slightly more than the diameter of each of the one or more rollers (e.g., rollers 544-1, 544-2, 544-3, 544-4, 544-5, 544-X in FIG. 5) to matching the depth of the portions of the concentric void 778-1, ..., 778-Q. The depth of the portions of the concentric void 778-1, ..., 778-Q are less than the diameter of each of the one or more rollers but sufficiently large enough to accommodate movement of the one or more spring tabs 776-1, ..., 766-M. The radial outer surface of the one or more spring tabs 776-1, ..., 766-M is sufficient to accommodate spring openings 768-1, ..., 768-N while allowing rotation in the cylindrical opening. The radial outer surface of tab 770 has a diameter sufficient to accommodate detent spring opening (e.g., detent spring opening 772 in FIG. 7A) while allowing rotation in the cylindrical opening.

Figure 8A:
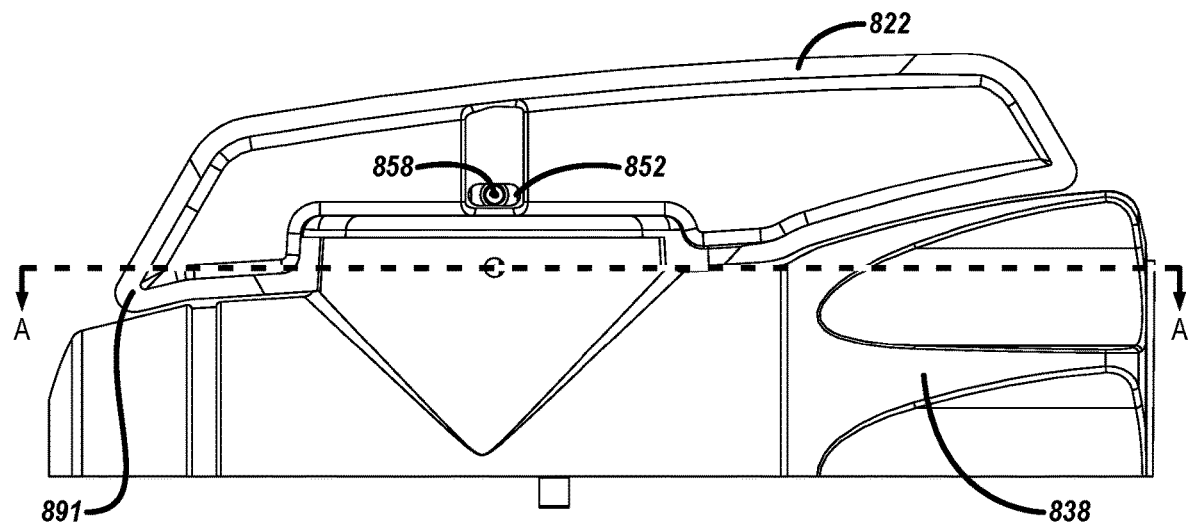
FIG. 8A is a side view of a knob and a top housing in accordance with a number of embodiments of the present disclosure.

FIG. 8A is a side view of a knob 822 and a top housing 838. FIG. 8A further illustrates an end of spring pin 858 located within knob opening 852 and tip 891 located at an end of knob 822.

Figure 8B:
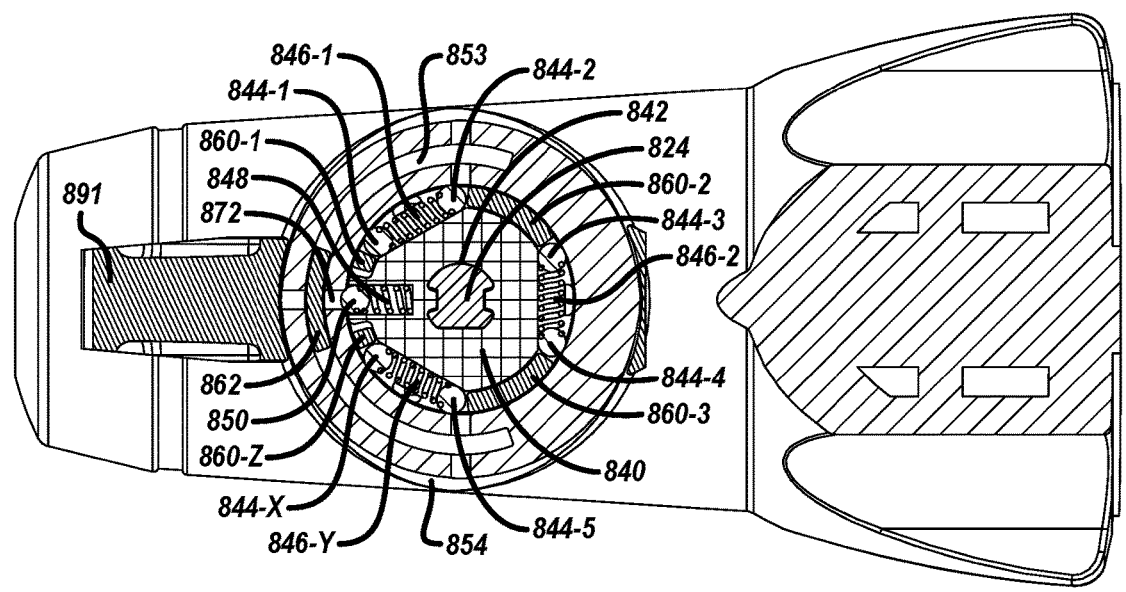
FIG. 8B is a section view of section A-A of FIG. 8A in accordance with a number of embodiments of the present disclosure.

FIG. 8B is a section view of section A-A of FIG. 8A. FIG. 8B illustrates stop tab 862, one or more tabs 860-1, 860-2, 860-3, 860-Z, detent spring 848, detent sphere 850, one or more rollers 844-1, 844-2, 844-3, 844-4, 844-5, 844-X, one or more roller springs 846-1, 846-2, 846-Y, a lock core 840 including spline 842, shaft of cam 824, cylindrical opening 854, detent opening 872, and tip 891.

The knob 822 can include stop tab 862. The stop tab 862 can be positioned within stop slot 853 of top housing 838. The length of stop slot 853 can limit the rotation of knob 822. For example, the knob will not be able to rotate past either end of stop slot 853.

Detent sphere 850, with outward force provided by detent spring 848, is shown in detent opening 872. The detent opening 872 can be sized smaller than the diameter of the detent sphere 850. When detent sphere 850 is positioned in detent opening 872, knob 822 and the distal end of the reloadable cartridge assembly (e.g., reloadable cartridge assembly 103 in FIG. 1) are parallel to the longitudinal axis of the reloadable cartridge. In some embodiments, when detent sphere 850 moves into detent opening 872, a tactile and/or auditory indication is provided to the user.

The one or more rollers 844-1, . . . , 844-X are positioned on either side of each of the one or more roller springs 846-1, . . . , 846-Y. For example, roller 844-1 is positioned on a first end of spring 846-1 and roller 844-2 is positioned on a second end of spring 846-1, roller 844-3 is positioned on a first end of spring 846-2 and roller 844-4 is positioned on a second end of spring 846-2, and roller 844-5 is positioned on a first end of spring 846-Y and roller 844-X is positioned on a second end of spring 846-Y. Each of the one or more roller springs 846-1, . . . , 846-Y provide a force that moves the one or more rollers 844-1, . . . , 844-X on either end of each of the one or more roller springs 846-1, . . . , 846-Y away from each other.

To articulate the reloadable cartridge assembly, the user will rotate knob 822. Rotation of knob 822 in a clockwise direction, will cause the one or more tabs 860-1, . . . , 860-Z to rotate and move the one or more rollers 844-2, . . . , 844-X in a clockwise direction, overcoming the force of the one or more roller springs 846-1, . . . , 846-Y. This clockwise movement can cause the one or more rollers 844-2, . . . , 844-X to move from the intersection of the jamming surfaces (e.g., jamming surfaces 776-1, . . . , 776-P in FIG. 7B) and the portions of concentric void (e.g., portions of the concentric void 778-1, . . . , 778-Q in FIG. 7B) into the larger depth portion of the jamming surfaces of lock core 840. For example, tab 860-1 will contact and apply force to roller 844-1 in response to the rotation of the knob 822 in the clockwise direction. Roller 844-1 will apply force to roller spring 846-1 in response to the applied force from tab 860-1 and roller spring 846-1 will apply force to roller 844-2 in response to the applied force from roller spring 846-1. As the roller 844-2 is pushed in a clockwise direction, the roller 844-2 pushes on jamming surface (e.g., jamming surface 776-1 in FIG. 7B) proximate to a portion of the concentric void (e.g., portion of the concentric void 778-1 in FIG. 7B). As the depth between the inner wall of cylindrical opening 854 and the intersection of the portion of the concentric void and the jamming surface is less than the diameter of the rollers 844-2, . . . , 844-X, the movement of the 844-2 roller will cause lock core 840 to move in a clockwise direction. This rotation of lock core 840 rotates cam 824 and causes sliding link (e.g., sliding link 234 in FIG. 2) and articulation arm (e.g., articulation arm 236 in FIG. 2) to move in a distal direction causing the distal end of the reloadable cartridge assembly to move in (e.g., rotate in) a clockwise direction.

Similarly, to articulate the reloadable cartridge assembly in a counterclockwise direction, the user can rotate the knob 822 in a counterclockwise direction. In some examples, rotation of knob 822 in a counterclockwise direction, will cause tab 860-2 to move roller 844-2 in a counterclockwise direction, overcoming the force of roller spring 846-1. This counterclockwise movement causes the roller 844-2 to move from the intersection of the jamming surface and concentric void into the larger depth portion of the jamming surface of lock core 840.

In a number of embodiments, continued counterclockwise rotation of knob 822 causes the 844-2 roller to continue pushing on roller springs 846-1 and the roller spring 846-1 to push on roller 844-1. As the 846-1 roller is pushed in a counterclockwise direction, the 846-1 roller pushes on the jamming surface proximate to a portion of the concentric void. As the depth between the inner wall of the cylindrical opening 854 and the intersection of the portion of the concentric void and the jamming surface is less than the diameter of the roller 846-1, the movement of the roller 846-1 will cause lock core 840 to move in a counterclockwise direction. This rotation of lock core 840 rotates cam 824 and causes sliding link 234 and articulation arm 236 to move in a proximal direction causing the distal end of the reloadable cartridge assembly to move in a counterclockwise direction.

The articulation assembly can maintain the reloadable cartridge assembly in an operation position. When the user stops rotating knob 822 and the knob 822 stops applying force onto the roller 844-1, the roller 844-1, due to the force of the roller spring 846-1, moves to a position where the roller 844-1 pushes on the jamming surface proximate to the portion of the concentric void and the roller 844-2, due to the force of the roller spring 846-1, moves to a position where the roller 844-2 pushes on the jamming surface distal to the portion of the concentric void. With the rollers 844-1 and 844-2 in these positions, the lock core 840 will not move in a clockwise or counterclockwise direction until a user rotates the knob 822. As such, the articulation assembly will maintain the knob 822 in its current position and the reloadable cartridge assembly in its current operation position.

Knob 822 can be rotated a distance before cam 824 begins to rotate by coupling the knob 822 to the shaft of cam 824 via a spring pin 858 located within the opening 852 in knob 822. As knob 822 begins to rotate, initially cam 824 and spring pin 858 stay stationary. Stationary spring pin 858 does not interfere with the rotation of knob 822 as opening 852 allows the knob 822 to rotate without interference from the spring pin 858. As described above, the cam 824 rotates in response to rotation of the lock core 840.

Figure 9:
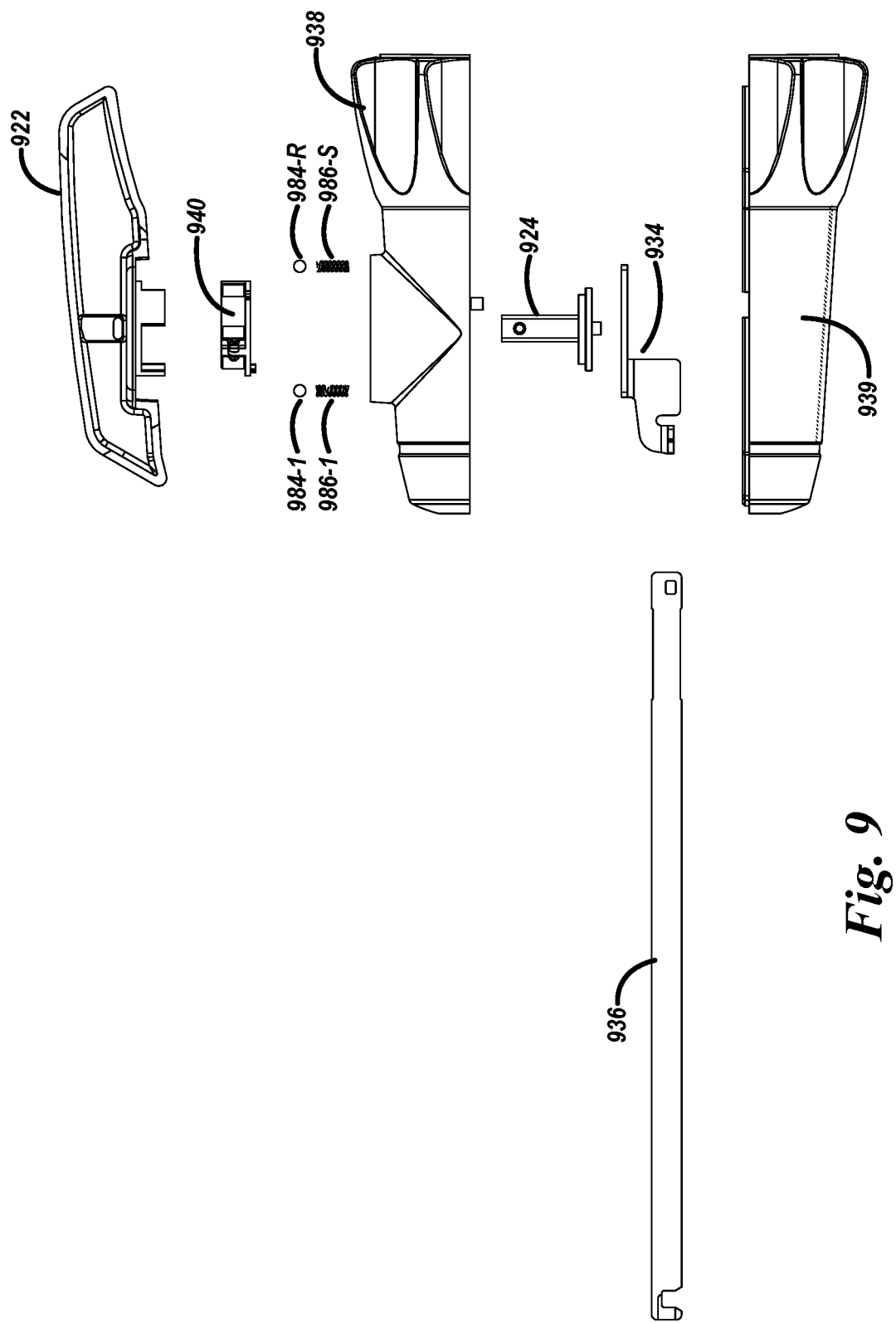
FIG. 9 is an exploded view of an articulation assembly in accordance with a number of embodiments of the present disclosure.

FIG. 9 is an exploded view of an articulation assembly in accordance with a number of embodiments of the present disclosure. The articulation assembly can include a knob 922, a cam 924, a lock core 940, a sliding link 934, an articulation arm 936, a top housing 938, and a bottom housing 939, which have been previously described in connection with FIG. 2. As illustrated in FIG. 9, the articulation assembly can further include one or more detent spheres 984-1 and 984-R and one or more detent springs 986-1 and 986-S.

The one or more detent spheres 984-1 and 984-R and the one or more detent springs 986-1 and 986-S can be used to indicate when the knob 922 and reloadable cartridge assembly (e.g., reloadable cartridge assembly 103 in FIG. 1) are aligned with the longitudinal axis of the reloadable cartridge. The top housing 938 can include one or more detent spring openings, not shown, for each of the one or more detent springs 986-1, 986-S. A portion of each of the one or more detent springs 986-1, 986-S can be located within the one or more detent spring openings. Each of the one or more detent springs can bias a detent sphere of the one or more detent spheres 984-1, 984-R into each of the one or more detent sphere openings in the knob 922 in response to the knob 922 being located at 0 degrees.

Figure 10:
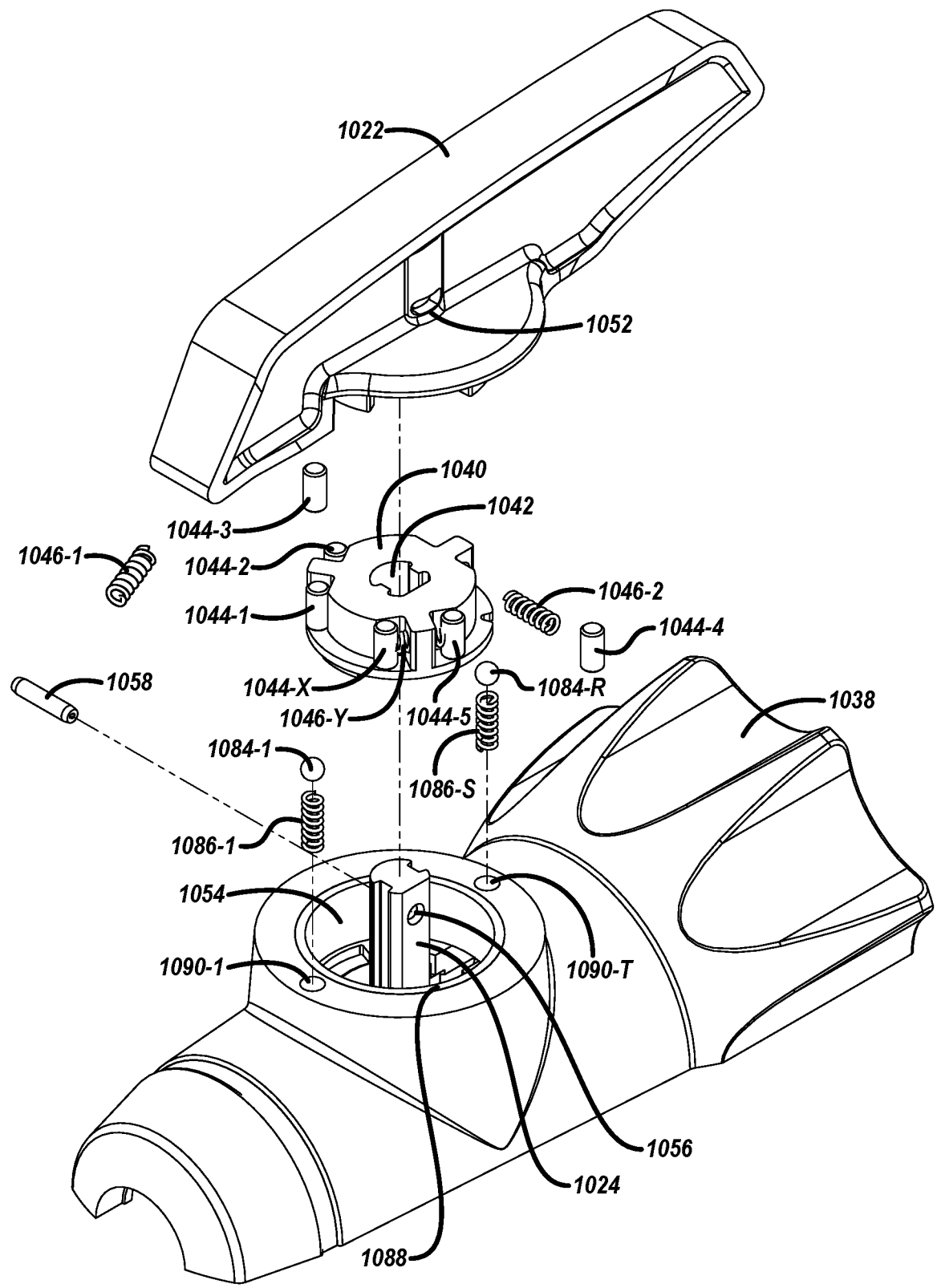
FIG. 10 is an exploded view of an articulation assembly in accordance with a number of embodiments of the present disclosure.

FIG. 10 is an exploded view of an articulation assembly in accordance with a number of embodiments of the present disclosure. The articulation assembly can include a knob 1022, a cam 1024, a lock core 1040, one or more roller springs 1046-1, 1046-2, 1046-Y, one or more rollers 1044-1, 1044-2, 1044-3, 1044-4, 1044-5, 1044-X, top housing 1038, a spring pin 1058, one or more detent spheres 1084-1, 1084-R, one or more detent springs 1086-1, 1086-S and a knob opening 1052, which have been previously described. The articulation assembly can further include a cylinder 1088 and one or more detent spring openings 1090-1, 1090-T.

Cylinder 1088 can be located within top housing 1038. For example, cylinder 1088 can be molded into cylindrical opening 1054 during manufacturing. In some examples, cylinder 1088 can be made from metal or plastic.

As previously described in connection with FIG. 9, the one or more detent spheres 1084-1 and 1084-R and the one or more detent springs 1086-1 and 1086-S can be used to indicate when the knob 1022 and reloadable cartridge assembly (e.g., reloadable cartridge assembly 103 in FIG. 1) are aligned with the longitudinal axis of the reloadable cartridge assembly. The knob 1022 can include one or more detent sphere openings (e.g., detent sphere openings 1192-1, 1192-V in FIG. 11) for each of the one or more detent spheres 1084-1, 1084-R and the top housing 838 can include one or more detent spring openings 1090-1, 1090-T for each of the one or more detent springs 1086-1, 1086-S. A portion of each of the one or more detent springs 1086-1, 1086-S can be located within the one or more detent spring openings. Each of the one or more detent springs 1086-1, 1086-S can bias a detent sphere of the one or more detent spheres 1084-1, 1084-R into each of the one or more detent sphere openings in the knob 1022 in response to the knob 1022 being located at 0 degrees. In some examples, when detent spheres 1084-1, 1084-R move into detent sphere openings, a tactile and/or auditory indication is provided to the user.

Figure 11A:
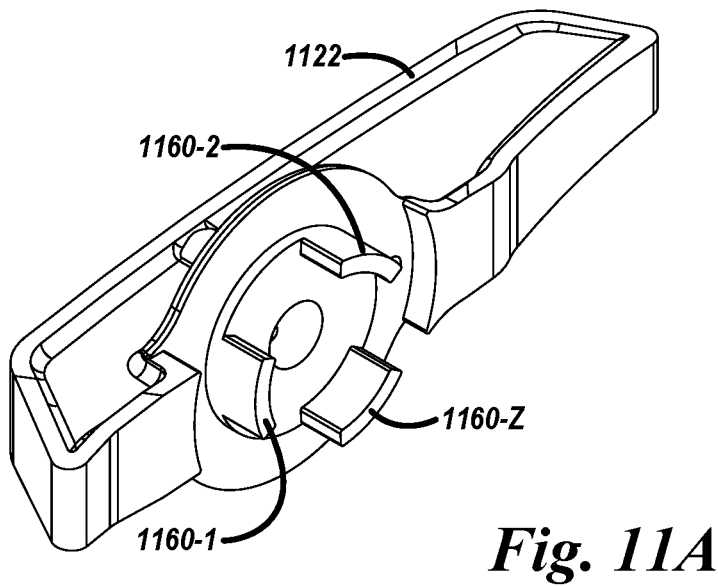
FIG. 11A is a perspective view of a knob in accordance with a number of embodiments of the present disclosure.

FIG. 11A is a perspective view of knob 1122 in accordance with a number of embodiments of the present disclosure. The bottom of knob 1122 includes one or more tabs 1160-1, 1160-2, 1160-Z. As illustrated in FIG. 11A, the knob can include, but is not limited to, three tabs 1160-1, 1160-2, 1160-Z that move one or more rollers (e.g., rollers 1044-1, . . . , 1044-X in FIG. 10).

Figure 11B:
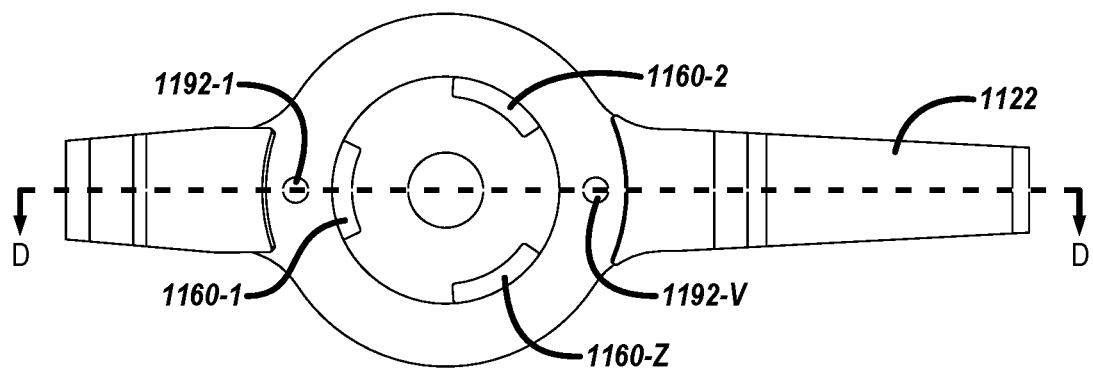
FIG. 11B is a bottom view of a knob in accordance with a number of embodiments of the present disclosure.

FIG. 11B is a bottom view of a knob 1122 in accordance with a number of embodiments of the present disclosure. Knob 1122 can include one or more tabs 1160-1, 1160-2, 1160-Z and one or more detent sphere openings 1192-1, 1192-V. Detent spheres (e.g., detent spheres 1084-1, 1084-R in FIG. 10) can fit into detent sphere openings 1192-1, 1192-V when knob 1122 is aligned with the longitudinal axis of the reloadable cartridge assembly. In some embodiments, when detent spheres move into detent sphere openings 1192-1, 1192-V, a tactile and/or auditory indication is provided to the user.

Figure 11C:
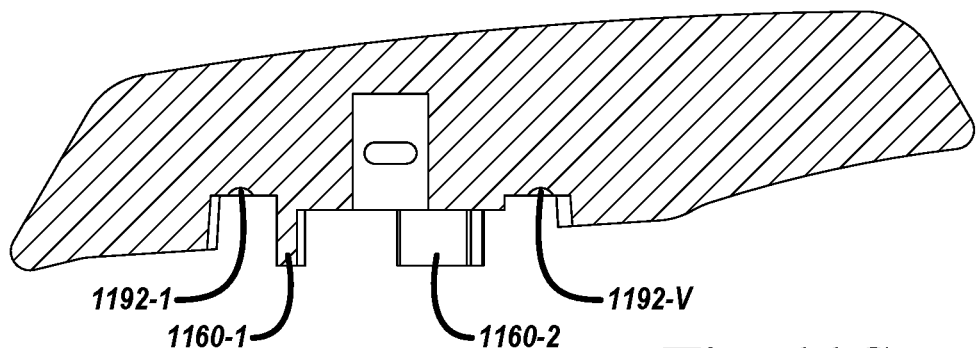
FIG. 11C is a section view of section D-D in FIG. 11B.

FIG. 11C is a section view of D-D in FIG. 11B. As illustrated in FIG. 11C, the knob 1122 can include one or more tabs 1160-1, 1160-2 and one or more detent openings 1192-1, 1192-V, as previously described in connection with FIG. 11B.

Figure 12A:
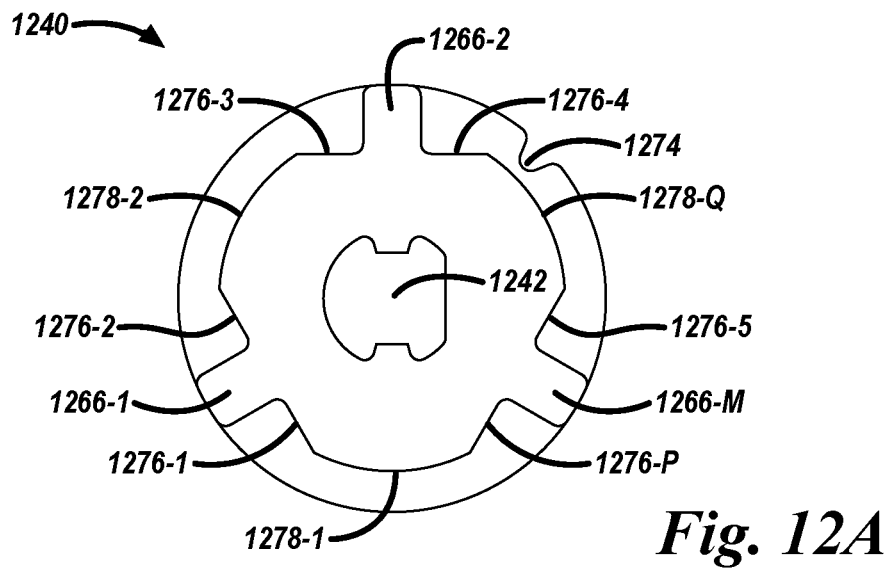
FIG. 12A is a top view of a lock core in accordance with a number of embodiments of the present disclosure.

FIG. 12A is a top view of a lock core 1240 in accordance with a number of embodiments of the present disclosure. The lock core 1240, as previously described in FIG. 7B, can include a spline 1242, jamming surfaces 1276-1, 1276-2, 1276-3, 1276-4, 1276-5, 1276-P, one or more spring tabs 1266-1, 1266-2, 1266-M, and portions of a concentric void 1278-1, 1278-2, 1278-Q. As illustrated in FIG. 12A, the lock core 1240 can include, but is not limited to, three spring tabs 1266-1, 1266-2, 1266-M.

Figure 12B:
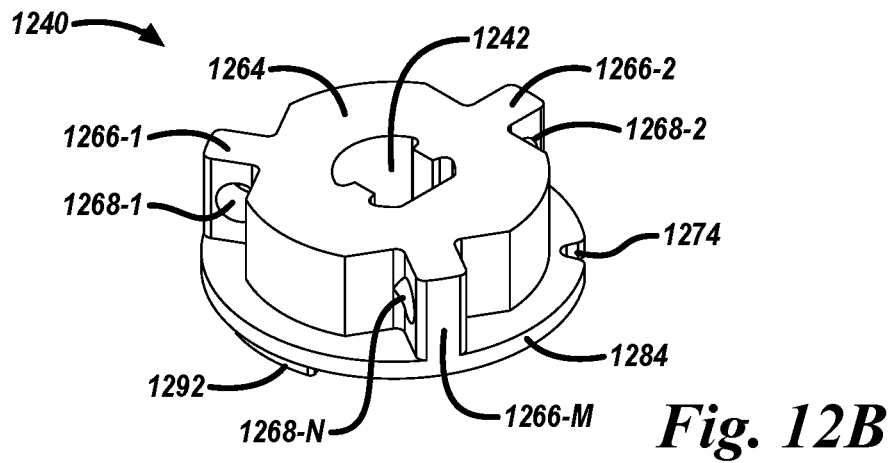
FIG. 12B is a perspective view of a lock core in accordance with a number of embodiments of the present disclosure.

FIG. 12B is a perspective view of a lock core 1240 in accordance with a number of embodiments of the present disclosure. The lock core 1240, as previously described in connection with FIG. 7A, can include a spline 1242, one or more spring tabs 1266-1, 1266-2, 1266-M, one or more roller spring openings 1268-1, 1268-2, 1268-N, a key 1274, a top portion 1264, and a bottom portion 1284. As illustrated in FIG. 12B, the lock core 1240 can include, but is not limited to, three spring tabs 1266-1, 1266-2, 1266-M.

Figure 12C:
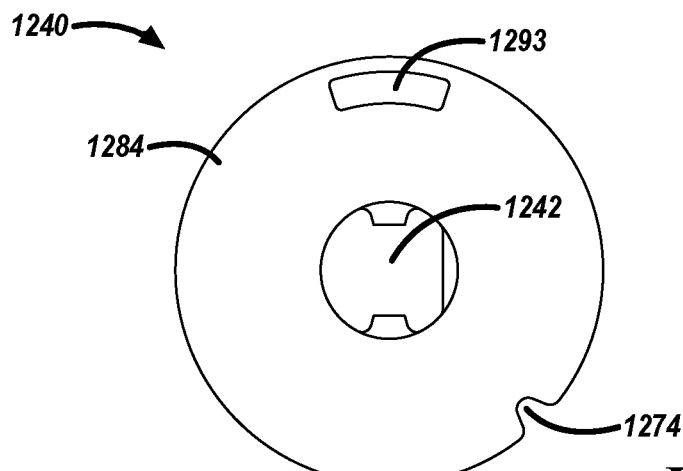
FIG. 12C is a bottom view of a lock core in accordance with a number of embodiments of the present disclosure.

FIG. 12C is a bottom view of a lock core 1240 in accordance with a number of embodiments of the present disclosure. The lock core 1240, as previously described in connection with FIG. 7A, can include a spline 1242, a bottom portion 1284, and a key 1274. As illustrated in FIG. 12C, the lock core 1240 can further include a stop lug 1293. The stop lug 1293 can be located in a groove (e.g., groove 1398 in FIG. 13C) to limit the rotation of lock core 1240, as will be further discussed in connection with FIG. 13C.

Figure 13A:
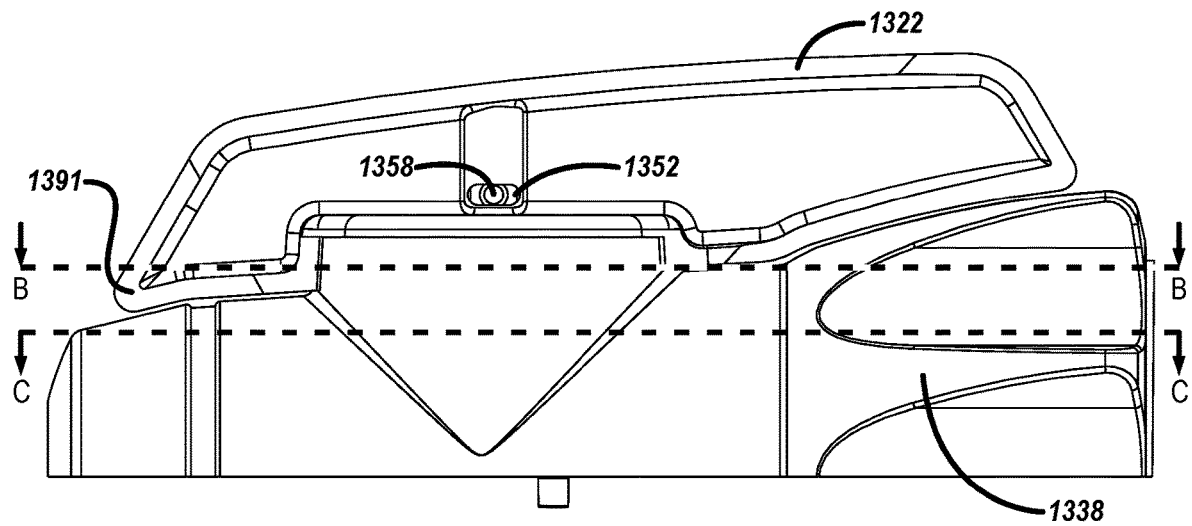
FIG. 13A is a side view of a knob and a top housing in accordance with a number of embodiments of the present disclosure.

FIG. 13A is a side view of a knob 1322 and a top housing 1338 in accordance with a number of embodiments of the present disclosure. FIG. 13A further illustrates an end of spring pin 1358 located within knob opening 1352 and tip 1391 located at an end of knob 1322.

Figure 13B:
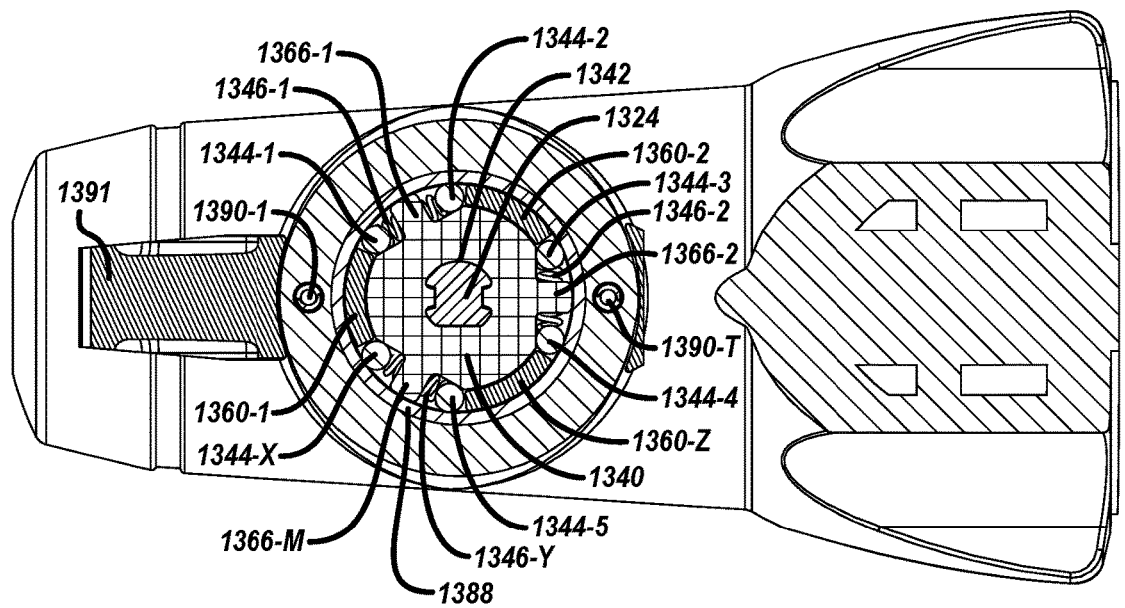
FIG. 13B is a section view of section B-B of FIG. 13A in accordance with a number of embodiments of the present disclosure.

FIG. 13B is a section view of section B-B of FIG. 13A in accordance with a number of embodiments of the present disclosure. As previously discussed in connection with FIG. 8B, an articulation assembly can include one or more tabs 1360-1, 1360-2, 1360-Z, one or more rollers 1344-1, 1344-2, 1344-3, 1344-4, 1344-5, 1344-X, one or more roller springs 1346-1, 1346-2, 1346-Y, a lock core 1340 including spline 1342, shaft of cam 1324, and tip 1391. FIG. 13B further includes a cylinder 1388 and one or more detent spring openings 1390-1, 1390-T, previously described in connection with FIG. 10.

Figure 13C:
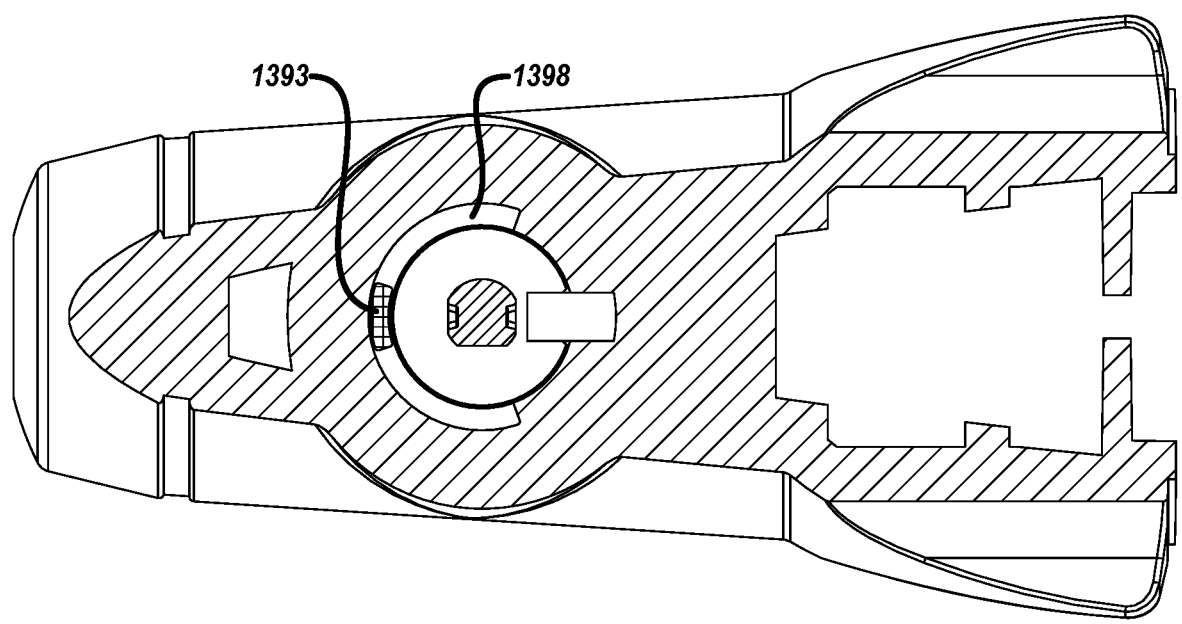
FIG. 13C is a section view of section C-C of FIG. 13A in accordance with a number of embodiments of the present disclosure.

FIG. 13C is a section view of section C-C of FIG. 13A in accordance with a number of embodiments of the present disclosure. Lock core 1340 includes stop lug 1393 and top housing 1338 includes groove 1398. As illustrated in FIG. 13C, stop lug 1393 is located within groove 1398. Stop tab 1397 being coupled to or a part of lock core 1340, limits the rotation of lock core 1340 and accordingly limits the rotation of knob 1322 and the reloadable cartridge assembly (e.g., reloadable cartridge assembly 103 in FIG. 1) in response to stop tab 1397 contacting an end of groove 1398.

In many prior art articulation mechanisms, the articulation of the medical device is limited to a certain number of discrete positions. In the embodiments disclosed herein, the mechanism can, subject to a stop if used or to the physical limitation of the mechanism, be articulated to any angle.

In many embodiments herein, the handle assembly (e.g., handle assembly 102 in FIG. 1) is shown as being manually actuated. Other handle assemblies such as ones that are driven by an electric motor may also be used. In these motor driven handle assemblies, a disposable or reusable/rechargeable battery may be used. It is also envisioned that the handle assembly could be replaced by a robotic or remotely controlled mechanism. In this embodiment, the physician/user is remote from the patient and controls the device from a computer input station or the like. In this embodiment, the reload cartridge assembly (e.g., reload cartridge assembly 103 in FIG. 1) would be connected to a robotic or remotely controlled arm.

In many embodiments herein, the reload cartridge assembly (e.g., reload cartridge assembly 103 in FIG. 1) is shown to include a connection to the handle assembly, a shaft, the jaw assembly including a first elongated member (e.g., elongated member 107 in FIG. 1) and a second elongated member (e.g., elongated member 109 in FIG. 1), a hinge component to accommodate the articulation of the jaw assembly, and an articulation joint, which can be mechanically connected to the articulation assemblies disclosed herein, which allows the distal end of the reload cartridge to be articulated. The inventions described herein are equally applicable to a configuration wherein the handle assembly (e.g., handle assembly 102 in FIG. 1) comprises the handle and the articulation mechanism and the articulation joint that allows for the articulation of the jaws. In this embodiment, the entire articulation mechanism (the mechanism and the joint) will be in the shaft of the handle assembly. In various embodiments, the reload cartridge could comprise a connector and the jaw assembly or just a staple cartridge.

Although specific embodiments have been illustrated and described herein, those of ordinary skill in the art will appreciate that an arrangement calculated to achieve the same results can be substituted for the specific embodiments shown. This disclosure is intended to cover adaptations or variations of one or more embodiments of the present disclosure. It is to be understood that the above description has been made in an illustrative fashion, and not a restrictive one. Combination of the above embodiments, and other embodiments not specifically described herein will be apparent to those of skill in the art upon reviewing the above description. The scope of the one or more embodiments of the present disclosure includes other applications in which the above structures and processes are used. Therefore, the scope of one or more embodiments of the present disclosure should be determined with reference to the appended claims, along with the full range of equivalents to which such claims are entitled.

In the foregoing Detailed Description, some features are grouped together in a single embodiment for the purpose of streamlining the disclosure. This method of disclosure is not to be interpreted as reflecting an intention that the disclosed embodiments of the present disclosure have to use more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. An apparatus, comprising:
a reloadable cartridge assembly; and
a surgical handle assembly including an articulation assembly configured to maintain the reloadable cartridge assembly in a first operation position, the articulation assembly comprising:
a knob in a first position;
a lock core coupled to the knob;
a housing;
a first roller and a second roller; and
a first spring, wherein the first roller is positioned on a first end of the first spring and the second roller is positioned on a second end of the first spring, and wherein the first spring is configured to bias the first roller and the second roller between the lock core and the housing to maintain the knob in the first position.

2. The apparatus of claim 1, wherein the articulation assembly is configured to maintain the reloadable cartridge assembly in one of a plurality of operation positions including the first operation position.

3. The apparatus of claim 1, wherein the articulation assembly further includes a cam coupled to the lock core.

4. The apparatus of claim 1, wherein the first roller and the second roller are metal.

5. The apparatus of claim 1, further comprising a third roller, a fourth roller, and a second spring, wherein the third roller is positioned on a first side of the second spring and the fourth roller is positioned on a second side of the second spring, wherein the second spring is configured to bias the third roller and the fourth roller between the lock core and the housing to maintain the knob in the first position.

6. The apparatus of claim 5, further comprising a fifth roller, a sixth roller, and a third spring, wherein the fifth roller is positioned on a first side of the third spring and the sixth roller is positioned on a second side of the third spring, wherein the third spring is configured to bias the fifth roller and the sixth roller between the lock core and the housing to maintain the knob in the first position.

7. An apparatus, comprising:
a reloadable cartridge assembly; and
a surgical handle assembly including an articulation assembly configured to actuate the reloadable cartridge assembly from a first operation position to a second operation position, the articulation assembly comprising:
a knob configured to rotate from a first knob position to a second knob position;
a lock core;
a housing;
a first roller and a second roller; and
a spring, wherein the first roller is positioned on a first side of the spring and the second roller is positioned on a second side of the spring, and wherein the spring is configured to bias the first roller and the second roller between the lock core and the housing and the first roller and the second roller are configured to rotate to allow the lock core to rotate with the knob.

8. The apparatus of claim 7, wherein the reloadable cartridge assembly is configured to rotate about an axis of a particular plane from the first operation position to a second operation position.

9. The apparatus of claim 7, wherein the knob is actuated to a third knob position and the reloadable cartridge assembly is actuated to a third operation position.

10. The apparatus of claim 7, wherein the knob is actuated clockwise from the first knob position to the second knob position to actuate the reloadable cartridge assembly clockwise from the first operation position to the second operation position.

11. The apparatus of claim 7, wherein the articulation assembly further includes a first tab and a second tab coupled to the knob.

12. The apparatus of claim 11, wherein the first tab is configured to contact the first roller in response to a rotation of the knob from the first knob position to the second knob position.

13. The apparatus of claim 11, wherein the second tab is configured to contact the second roller in response to a rotation of the knob from the second knob position to the first knob position.

14. A method of articulating a medical device comprising:
   providing the medical device, including:
      a housing;
      a knob having a tab;
      a lock core, wherein the lock core includes a spline;
      a cam coupled to the lock core via the spline, wherein the cam includes a pin member;
      a first roller and a second roller; and
      a spring, wherein the first roller is positioned on a first side of the spring and the second roller is positioned on a second side of the spring, and wherein the spring is configured to bias the first roller and the second roller between the lock core and the housing;
   rotating the knob;
   contacting the first roller with the tab in response to rotating the knob;
   rotating the first roller and the second roller in response to the tab contacting the first roller;
   rotating the lock core in response to rotating the first roller and the second roller;
   rotating the cam in response to rotating the lock core; and
   moving the pin member of the cam linearly in response to rotating the cam.

15. The method of claim 14, wherein the medical device further includes a sliding link with a slot, wherein the pin member of the cam is positioned within the slot.

16. The method of claim 15, further comprising moving the sliding link linearly in response to the pin member of the cam moving linearly.

17. The method of claim 16, wherein the medical device further includes an articulation arm coupled to the sliding link.

18. The method of claim 17, further comprising moving the articulation arm linearly in response to the sliding link moving linearly.

19. The method of claim 18, wherein the medical device further includes a reloadable cartridge assembly.

20. The method of claim 19, further comprising rotating the reloadable cartridge assembly in response to the articulation arm moving linearly.

* * * * *